(12) United States Patent
Coppola

(10) Patent No.: US 6,710,182 B2
(45) Date of Patent: Mar. 23, 2004

(54) PROCESS FOR THE PREPARATION OF THIAZOLE DERIVATIVES

(75) Inventor: Kevin Coppola, Baton Rouge, LA (US)

(73) Assignee: Syngenta Crop Protection, Inc., Greensboro, NC (US)

(*) Notice: Subject to any disclaimer, the term of this patent is extended or adjusted under 35 U.S.C. 154(b) by 0 days.

(21) Appl. No.: 10/431,100

(22) Filed: May 7, 2003

(65) Prior Publication Data

US 2003/0191321 A1 Oct. 9, 2003

Related U.S. Application Data

(62) Division of application No. 10/244,236, filed on Sep. 16, 2002, now Pat. No. 6,566,530, which is a division of application No. 10/049,073, filed as application No. PCT/EP00/07709, and a division of application No. 09/371,180, filed on Oct. 8, 1999, now Pat. No. 6,265,553.

(51) Int. Cl.$^7$ ............................................. C07D 277/02
(52) U.S. Cl. ..................................................... 548/202
(58) Field of Search ........................................ 548/202

(56) References Cited

U.S. PATENT DOCUMENTS

| | | | |
|---|---|---|---|
| 4,748,243 A | * | 5/1988 | Beck et al. ................. 548/202 |
| 5,773,625 A | | 6/1998 | Langridge |
| 6,407,251 B1 | * | 6/2002 | Miyazaki et al. ........... 548/202 |

* cited by examiner

Primary Examiner—Robert W. Ramsuer
(74) Attorney, Agent, or Firm—Rose M. Allen

(57) ABSTRACT

The present invention relates to intermediate thiazole compounds and a process for preparing 2-chloro-5-chloromethylthiazole which is a known compound useful for the preparation of insecticides.

1 Claim, No Drawings

PROCESS FOR THE PREPARATION OF THIAZOLE DERIVATIVES

This application is a division of Ser. No. 10/244,236 filed Sep. 16, 2002 now U.S. Pat. No. 6,566,530 which is a division of Ser. No. 10/049,073 filed Feb. 4, 2002 now U.S. Pat. No. 6,476,230, which is the national stage of PCT/EP00/07709 filed Aug. 8, 2000 and a division of Ser. No. 09/371,180 filed Oct. 8, 1999, now U.S. Pat. No. 6,265,553.

FIELD OF THE INVENTION

The present invention relates to intermediate thiazole compounds and a process for preparing 2-chloro-5-chloromethyl-thiazole which is a known compound useful for the preparation of insecticides.

BACKGROUND OF THE INVENTION

The compound 2-chloro-5-chloromethyl-thiazole is known intermediate useful for the preparation of insecticides. See European patent application No. 192,060. U.S. Pat. No. 4,748,243 to Beck et al. and EP 448,913 describe a process of preparing 2-chloro-5-chloromethyl-thiazole by reaction certain allyl isocyanates with chlorine.

SUMMARY OF THE INVENTION

Surprisingly, it has now been discovered that 2-chloro-5-chloromethylthiazole may be conveniently prepared from 2-chloro-5-hydroxymethylthiazole, 2-hydroxy-5-hydroxymethylthiazole or a 5-hydroxymethylthiazol-2-diazonium salt compound. These processes avoid the costs and hazards of using allyl isocyanate reagents and chlorine. Additionally, it has been discovered that 2-chloro-5-hydroxymethylthiazole and 2-hydroxy-5-hydroxymethylthiazole may be prepared via a 5-hydroxymethylthiazol-2-diazonium intermediate. Surprisingly, it has also been discovered that the 2-chloro-5-hydroxymethylthiazole, the 2-hydroxy-5-hydroxymethylthiazole or the 5-hydroxymethylthiazol-2-diazonium salts may be derived from 2-amino-5-hydroxymethylthiazole which is a known compound.

DETAILED DESCRIPTION OF THE INVENTION

One embodiment of the invention is the compound 2-hydroxy-5-hydroxymethylthiazole having the formula:

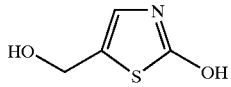

(and acid addition salts thereof) which is also useful for making 2-chloro-5-chloromethylthiazole.

It is recognized that salts 2-hydroxy-5-hydroxymethylthiazole are also similarly useful intermediates and are part of the instantly disclosed invention. For example, the hydrochloride salts of 2-chloro-5-hydroxymethylthiazole and 2-hydroxy-5-hydroxymethylthiazole also are useful intermediates for preparing 2-chloro-5-chloromethylthiazole.

Another embodiment of the invention is 5-hydroxymethylthiazolyl-2-diazonium salt of formula:

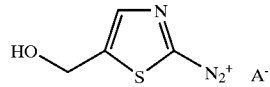

(and acid addition salts thereof) wherein $A^-$ is a counter-anion derived from an acid HA, wherein HA is an organic acid or inorganic mineral acid. The organic acid for example may be formic acid, acetic acid, or benzoic acid. The inorganic acid for example may be a halogen acid, sulfuric acid, nitric acid, or phosphoric acid. Preferably $A^-$ is a halogen anion, an anion of the formula $^-OSO_2R_1$ wherein $R_1$ is $C_1$–$C_4$ alkyl, phenyl, $C_7$–$C_{10}$-alkylaryl, or $C_5$–$C_{10}$ cycloalkyl; or an anion of the formula $^-OOC$—$R_2$ wherein $R_2$ is $C_1$–$C_4$-haloalkyl or $R_1$. The diazonium salts are useful for making 2-chloro-5-hydroxymethylthiazole, 2-hydroxy-5-hydroxymethylthiazole and 2-chloro-5-chloromethylthiazole.

Another embodiment of the invention is the process for making 2-chloro-5-chloromethylthiazole (and acid addition salts thereof) comprising the step of reacting the known 2-chloro-5-hydroxymethylthiazole, or 2-hydroxy-5-hydroxymethylthiazole or a 5-hydroxymethylthiazolyl-2-diazonium salt with a chloride anion source in the presence of an acid. The chloride anion source is not limited to but may be selected from the group consisting of an inorganic acid, a chloride salt, an acyl chloride and a sulfonyl chloride. The inorganic acid acting as the chloride anion source for example may be HCl, $SOCl_2$, $PCl_3$, $POCl_3$, or $PCl_5$. The chloride salt may be for example NaCl, KCl, $CaCl_2$, ammonium chloride or a mono-, di-, tri-, tetra-alkylammonium chloride. The acyl chloride for example may be acetyl chloride or benzoyl chloride; or for example a chloroformate or a thiochloroformate such as ethyl chloroformate or ethyl thiochloroformate. The sulfonyl chloride for example may be mesyl chloride or tosyl chloride. It will be recognized that when the starting reagent is a hydrochloride addition salt or is 5-hydroxymethylthiazolyl-2-diazonium chloride salt, the starting reagent itself will serve also as a chloride anion source.

The skilled artisan will realize that the presence of acid in the reaction medium may be generated in situ from the reaction of the appropriate chloride anion source with the 2-chloro-5-hydroxymethylthiazole, 2-hydroxy-5-hydroxymethylthiazole or any hydroxylic solvent that may be present in the reaction medium. The presence of acid in the reaction medium may also be provided by the addition of an organic acid or an inorganic acid. The organic acid for example may be formic acid, acetic acid, or benzoic acid. The inorganic acid for example may be a halogen acid, sulfuric acid, nitric acid, sulfur trioxide, phosphoric acid or phosphorous pentoxide.

The process may preferably be conducted in the presence of a solvent. The solvent for example may be hexane, cyclohexane, chloroform, methylene chloride, diethyl ether, tetrahydrofuran, toluene, or water, or mixtures thereof. When water is present other by-products may result due to the hydrolysis. The process may also be advantageously conducted under reflux conditions.

Another embodiment of the invention is the process for making 2-chloro-5-hydroxymethylthiazole (and acid addition salts thereof) comprising the step of reacting 2-amino-5-hydroxymethylthiazole (and acid addition salts thereof) with an alkali metal nitrite in the presence of an acid and in the presence of a chloride anion source. The alkali metal nitrite may be either sodium nitrite or potassium nitrite. The presence of a chloride anion source may be obtained by addition of the chloride anion source described above. The presence of acid in the reaction medium may be achieved in a similar fashion as discussed above for preparing 2-chloro-5-chloromethylthiazole. Thus it will be recognized that under the appropriate reaction conditions (e.g. temperature, pressure, concentration, reaction time etc.), 2-chloro-5-chloromethylthiazole may be prepared directly from 2-amino-5-hydroxymethylthiazole without isolating or purifying the intermediate 2-chloro-5-hydroxymethylthiazole.

Another embodiment of the invention is the process for making 2-chloro-5-hydroxymethylthiazole (and acid addition salts thereof) comprising the step of reacting a 5-hydroxymethylthiazolyl-2-diazonium salt with a chloride anion source in the presence of an acid. The reaction conditions regarding the chloride anion source and the presence of acid are the same or similar to those used for the preparation of 2-chloro-5-chloromethylthiazole discussed above. It will be recognized that when the 5-hydroxymethylthiazolyl-2-diazonium chloride salt (or hydrochloride salt thereof) is used it will serve also as a chloride anion source.

Another embodiment of the invention is the process for making 2-hydroxy-5-hydroxymethylthiazole (and acid addition salts thereof) comprising the step of reacting 2-amino-5-hydroxymethylthiazole (and acid addition salts thereof) with an alkali metal nitrite in the presence of water. The alkali metal nitrite may be either sodium nitrite or potassium nitrite. The presence of a water may be obtained by addition of water or the water may be carried into the reaction from the previous reaction step(s) for preparing the 2-amino-5-hydroxymethylthiazole. Thus it will be recognized that the further addition of a chloride anion source in the presence of acid may be used to prepare 2-chloro-5-chloromethylthiazole directly from 2-amino-5-hydroxymethylthiazole without isolating or purifying the intermediate 2-hydroxy-5-hydroxymethylthiazole.

Another embodiment of the invention is the process for making 2-hydroxy-5-hydroxymethylthiazole (and acid addition salts thereof) comprising the step of reacting a 5-hydroxymethylthiazolyl-2-diazonium salt with water.

Another embodiment of the invention is the process for making the 5-hydroxymethylthiazolyl-2-diazonium salt of formula (1) (and acid addition salts thereof) comprising the step of reacting 2-amino-5-hydroxymethylthiazole with an alkali metal nitrite in the presence of acid. The alkali metal nitrite may be either sodium nitrite or potassium nitrite. The presence of acid in the reaction medium may be achieved in a similar fashion as discussed above for preparing 2-chloro-5-chloromethylthiazole. Thus it will be appreciated that by the further addition of a chloride anion source and with other appropriate reaction conditions (e.g. temperature, pressure, concentration, reaction time etc.), 2-chloro-5-chloromethylthiazole may be prepared directly from 2-amino-5-hydroxymethylthiazole without isolating or purifying the intermediate a 5-hydroxymethylthiazolyl-2-diazonium salt. It will be recognized that the 5-hydroxymethylthiazolyl-2-diazonium chloride salt (or hydrochloride salt thereof) may serve also as a chloride anion source.

Another aspect of the invention is the product produced from the process of diazotizing 2-amino-5-hydroxythiazole (and addition salts thereof) with aqueous alkali metal nitrite. The 5-hydroxymethylthiazolyl-2-diazonium salt of formula (1) or the product from the process of diazotization (to the extent there is a difference) are both features of the instantly disclosed invention. The scope of the invention as to the diazonium salts and the process of preparing the compound of formula (1) disclosed herein should not be construed to be limited by any particular chemical theory relating to the complexation, equilibration, reaction or acid-base chemistry of the components used to make the diazonium salt or the final product. Another aspect of the invention is a 5-hydroxymethylthiazolyl-2-diazonium salt of formula (1) wherein said salt has interacted chemically so as to result in a changed form of the salt or has interacted with other chemical components so as to form another more stable compound or acid addition salt thereof. Accordingly, the present invention encompasses the substantially unaltered static composition of the appropriate components as well as the chemically integrated composition. "Static composition" denotes 1) the composition composed of components wherein the components have not substantially changed by virtue of their combination or interaction with other composition components, or 2) the composition that has reacted to a point of relative stasis. "Chemically integrated composition" means a composition that results from any equilibration, complexation, dissociation or other chemical transformation (if any) that may occur after combination of the reagents used to prepare the product composition containing the salts of formula (1) and prior to ultimate use for the preparation of 2-chloro-5-hydroxymethylthiazole, 2-chloro-5-chloromethylthiazole and 2-hydroxy-5-hydroxymethylthiazole. Therefore, the "chemically integrated composition" of the instant invention by definition encompasses the situation where there is an unchanged "static composition" as well as the equilibrated or semi equilibrated composition existing at any point between initial creation and ultimate use. In other words, the disclosed invention relating to diazonium salts is not limited to a static composition of chemically unaltered constituent components.

Another embodiment of the invention is the process for making 2-amino-5-hydroxymethylthiazole (and acid addition salts thereof) comprising the step of reacting epoxypropanal with thiourea, preferably in an aqueous solvent system. The epoxypropanal is a known compound and may be prepared for example by reacting acrolein with an epoxidizing agent, preferably in an aqueous solvent system. The peroxides that are suitable epoxidizing agents are known and include hydrogen peroxide, alkylhydroperoxides, dialkylperoxides, peracids and peracid anhydrides. Examples of peracids include peracetic acid and perbenzoic acid.

Another aspect of the instant invention is the preparation of 2-amino-5-hydroxythiazole directly from acrolein by reaction with a peroxide followed by reaction with thiourea, without isolating or purifying the intermediate epoxypropanal. The reaction is preferably conducted under aqueous solvent conditions.

By "addition salts" are meant salts of a given compound (or salt) of the invention derived from the chemical interaction with inorganic acids or organic acids. Acid addition salts may also be adducts with an organic solvent or water.

Examples of acid addition salts derived from inorganic acids include hydrochlorides, hydrobromides, hydroiodides, sulfates, hydrogensulfates, phosphates, monohydrogenphosphates, dihydrogenphosphates, nitrates, and thiocyanates. Examples of acid addition salts derived from organic acids include carboxylates, sulfonates, and phosphonates. Examples of acid addition salts derived from a carboxylic acid include formates, acetates, propionates, butyrates, cinnamates, benzoates, lactates, oxalates, malonates, succinates, glutarates, adipates, maleates, fumarates, phthalates, citrates, tartarates, salicylates, nicotinates, mandelates and salts from amino acids. Examples of acid addition salts derived from a sulfonic acid include alkylsulfonates (e.g. methanesulfonates, benzenesulfonates (e.g. p-toluenesulfonates), naphthlenesulfonates and camphorsulfonates. Examples of acid addition salts derived from a phosphonic acid include alkylphosphonates (e.g. methylphosphonates) and benzenephosphonates (e.g. phenylphosphonates).

By "alkyl" is meant a $C_1$–$C_{10}$ alkyl group which is linear or branched. Examples of suitable alkyl groups include methyl, ethyl, n-propyl, iso-propyl, n-butyl, iso-butyl, sec-butyl, tert-butyl, neo-pentyl, n-hexyl, n-octyl and n-decyl.

Scheme I (below) provides an additional description of some of the embodiments of the invention and their interrelationship.

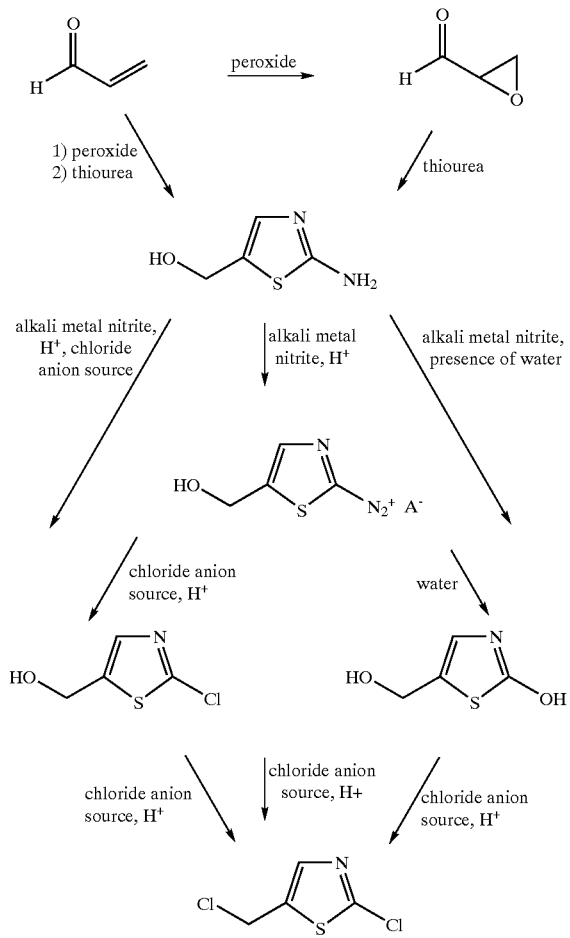

The following examples illustrate further some of the specific features of the invention but are not intended to limit its scope. Where not otherwise specified throughout this specification and claims, temperatures are given in degrees centigrade.

EXAMPLE 1

Preparation of Epoxypropanal

A solution of 800 ml water and 118 g. of 30% hydrogen peroxide (1.04 mole) was adjusted to a pH of 8.0–8.5 and cooled to 10° C. While maintaining a pH of 8–8.5 and a temperature of 10–20° C., 56 g (1.00 mole) of acrolein is added dropwise. The aqueous solution of the epoxy propanal must be kept cold until it is used directly to make 2-amino-5-hydroxymethylthiazole. The product may also be isolated using known procedures.

EXAMPLE 2

Preparation of 2-Amino-5-hydroxymethylthiazole

The epoxy propanal solution from example 1 is cooled to 0° C. With vigorous stirring, 76 g (1.00 mole) of thiourea was added in portions. After the addition is complete the water is removed under vacuum on a rotatory evaporator. An oil is isolated as the product (91.3 g).

EXAMPLE 3

Preparation of 5-Hydroxymethylthiazole-2-diazonium Chloride Salt

A reactor vessel is charged with 2-amino-2-hydroxymethylthiazole (1.0 moles, in a concentrated hydrochloric acid solution). The solution is cooled to 0° C. and sodium nitrite (1.1 equiv., in a concentrated hydrochloric acid solution) is added drop-wise to the reactor vessel with vigorous agitation of the reaction while maintaining the temperature in the range 0° C. to 20° C. After the addition is complete the reaction medium is maintained at 0° C. with stirring for 3 hours. Excess nitrous acid is then quenched by addition of urea. The product 5-hydroxymethylthiazole-2-diazonium salt may be isolated using known extraction and solvent removal procedures or the reaction product may be used directly to prepare 2-chloro-5-hydroxylmethylthiazole, 2-hydroxy-5-hydroxylmethylthiazole or 2-chloro-5-chloromethylthiazole.

EXAMPLE 4

Preparation of 2-Chloro-5-hydroxylmethylthiazole

One liter of the aqueous solution from example 2 (containing approximately 0.6 moles of amino-hydroxymethylthiazole) was mixed with 35 ml. of concentrated hydrochloric acid to achieve a pH of 3. The solution was chilled to 0° C., and sodium nitrite (30 g, 0.45 moles) was added in portions. The solution was maintained at 0° C. while an additional 15 ml. of concentrated hydrochloric acid was added dropwise. Cuprous chloride (35 g) was added, and the mixture was heated to 48° C. for 1 hour. Upon cooling, the solution was filtered. Acetic anhydride (100 g) and urea (10 g) were added. The solution was extracted with butanol. Butanol extract furnished 2-chloro-5-hydroxylmethylthiazole.

EXAMPLE 5

Preparation of 2-Chloro-5-chloromethylthiazole

A 1.00 mole batch of 2-amino-5-hydroxymethylthiazole was prepared in water as described above in Example 2. The water was removed by rotory evaporation, and the residue was dissolved in 500 ml. of concentrated HCl. The solution was cooled to between −5 and 5° C., then 1.00 mole of sodium nitrite was added in portions. The temperature of the reaction solution increased to 11° C. after an exotherm. The solution was then allowed to stir for 2 hours. Twenty grams of urea was added, followed by 50 ml of concentrated nitric acid. The solution was cooled to 0° C. and 8 g of copper metal was added and the solution was stirred overnight. The mixture was extracted 3 times with methybutylketone. The solvent was removed by rotary evaporation to yield an oil (18 g.) that was identified by GC MS as 2-chloro-5-chloromethylthiazole.

In summary, it is seen that this invention provides new intermediates that are useful for preparing the 2-chloro-5-chloromethylthiazole which is an intermediate that is known to be useful for preparing insecticides. The invention also encompasses the processes for making the intermediates used to make 2-chloro-5-chloromethylthiazole. Variations may be made in proportions, procedures and materials without departing from the scope of the invention as defined by the following claims.

What is claimed is:

1. A process for preparing the compound having the formula:

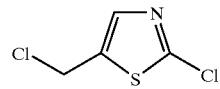

and acid addition salts thereof, comprising the step of reacting the 5-hydroxymethylthiazole-diazonium salt of formula

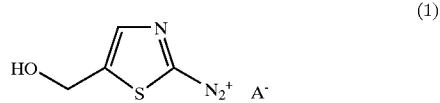

(1)

wherein A⁻ is a counter-anion derived from an acid HA, wherein HA is an organic acid or inorganic mineral acid, with chloride anion source in the presence of acid.

* * * * *